United States Patent
Fallin et al.

(10) Patent No.: US 11,207,307 B2
(45) Date of Patent: Dec. 28, 2021

(54) COMPOSITION AND METHOD FOR PROTON PUMP INHIBITOR SUSPENSION

(71) Applicant: CutisPharma, Inc., Wilmington, MA (US)

(72) Inventors: Ken Fallin, Diamondhead, MS (US); Kaity Renaud, Melrose, MA (US); Peter Mione, Malden, MA (US); Neal Muni, Wellesley, MA (US); Anisa Gandhi, Medford, MA (US)

(73) Assignee: AZURITY PHARMACEUTICALS, INC., Woburn, MA (US)

( * ) Notice: Subject to any disclaimer, the term of this patent is extended or adjusted under 35 U.S.C. 154(b) by 0 days.

(21) Appl. No.: 16/310,675

(22) PCT Filed: Jun. 16, 2017

(86) PCT No.: PCT/US2017/037875
§ 371 (c)(1),
(2) Date: Dec. 17, 2018

(87) PCT Pub. No.: WO2017/218894
PCT Pub. Date: Dec. 21, 2017

(65) Prior Publication Data
US 2019/0321348 A1    Oct. 24, 2019

Related U.S. Application Data

(60) Provisional application No. 62/351,271, filed on Jun. 16, 2016.

(51) Int. Cl.
| | | |
|---|---|---|
| *A61K 31/4439* | (2006.01) | |
| *A61K 9/00* | (2006.01) | |
| *A61K 47/10* | (2017.01) | |
| *A61K 47/12* | (2006.01) | |
| *A61K 47/20* | (2006.01) | |
| *A61K 47/26* | (2006.01) | |
| *A61K 47/38* | (2006.01) | |
| *A61K 45/06* | (2006.01) | |

(52) U.S. Cl.
CPC ........ *A61K 31/4439* (2013.01); *A61K 9/0095* (2013.01); *A61K 47/10* (2013.01); *A61K 47/12* (2013.01); *A61K 47/20* (2013.01); *A61K 47/26* (2013.01); *A61K 47/38* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 5,658,919 A | * | 8/1997 | Ratnaraj | A61K 9/0095 514/269 |
| 5,763,449 A | * | 6/1998 | Anaebonam | A61K 9/0095 514/179 |
| 6,645,988 B2 | | 11/2003 | Phillips | |
| 7,300,670 B2 | * | 11/2007 | Venus | A61K 9/0095 424/400 |
| 7,815,933 B2 | | 10/2010 | Holmberg | |
| 10,751,333 B1 | | 8/2020 | Pendon et al. | |
| 2004/0191276 A1 | | 9/2004 | Muni | |
| 2004/0192763 A1 | | 9/2004 | Chenard et al. | |
| 2005/0142271 A1 | | 6/2005 | Ojima et al. | |
| 2006/0094787 A1 | * | 5/2006 | Forenzo | A61K 9/0095 514/567 |
| 2008/0299211 A1 | * | 12/2008 | Chrzan | A61K 31/445 424/499 |
| 2010/0015184 A1 | | 1/2010 | Tuel | |
| 2010/0323020 A1 | | 12/2010 | Gokhale et al. | |
| 2013/0009311 A1 | | 1/2013 | Lin et al. | |
| 2014/0371242 A1 | | 12/2014 | Wang | |
| 2015/0216806 A1 | | 8/2015 | Borody | |
| 2015/0238613 A1 | | 8/2015 | Lin et al. | |
| 2016/0051684 A1 | | 2/2016 | Wang | |
| 2016/0361320 A1 | | 12/2016 | Zhao et al. | |
| 2017/0065671 A1 | | 3/2017 | Maher | |

FOREIGN PATENT DOCUMENTS

| | | |
|---|---|---|
| WO | WO-0103707 A1 | 1/2001 |
| WO | WO 2004/080451 A1 | 9/2004 |
| WO | WO-2004080541 A1 | 9/2004 |
| WO | WO 2008/048018 A1 | 4/2008 |
| WO | WO-2021011669 A1 | 1/2021 |

OTHER PUBLICATIONS

First-Omeprazole info, Nov. 2012 (Year: 2012).*
Moschwitzer, European Journal of Pharmaceutics and Biopharmaceutics, 58, 2004 (Year: 2004).*
Mathew, Drug Development and Industrial Pharmacy, 21, 8, 1995 (Year: 1995).*
International Search Report and Written Opinion for PCT/US2017/037875 dated Jul. 19, 2017.
International Preliminary Report on Patentability for PCT/US2017/037875 dated Dec. 27, 2018.
[No Author Listed], Process for preparing posaconazole oral suspension. IP.com Journal. 2013, 13(5B), 1 (No. IPCOM000227453D). 2 pages.
Cutispharma, Inc., Omeprazole, Omeprazole 2mg/mL in FIRST®-PPI Suspension Compounding Kit, Ingredients, published Dec. 7, 2015 as per Wayback Machine. Retrieved from the internet on Jul. 13, 2017. URL: <https://web.archive.org/web/20151207113010/http://www.cutispharma.com:80/products/oral-solutions-suspensions/ppis/omeprazole>.

(Continued)

*Primary Examiner* — Robert A Wax
*Assistant Examiner* — William Craigo
(74) *Attorney, Agent, or Firm* — Wilson Sonsini Goodrich & Rosati

(57) ABSTRACT

Suspensions of pump inhibitors (PPIs) are disclosed. The suspension may include a PPI, a copolymer of ethylene oxide and propylene oxide; simethicone emulsion; Sodium Bicarbonate; and Sodium Citrate, USP (Dihydrate). The suspensions have desirable viscosities and enhanced stability.

17 Claims, No Drawings

(56) References Cited

OTHER PUBLICATIONS

Bogman et al., P-glycoprotein and surfactants: effect on intestinal talinolol absorption. Clin Pharmacol Ther. Jan. 2005;77(1):24-32.
Castell, D., Review of immediate-release omeprazole for the treatment of gastric acid-related disorders. Expert Opin Pharmacother. Nov. 2005,6(14).2501-10.
Fischer et al., Effect of the non-ionic surfactant Poloxamer 188 on passive permeability of poorly soluble drugs across Caco-2 cell monolayers. Eur J Pharm Biopharm. Oct. 2011;79(2):416-22. doi: 10.1016/j.ejpb.2011.04.010. Epub Apr. 28, 2011.
Johnson, C.E., et al., Stability of partial doses of omeprazole-sodium bicarbonate oral suspension. Ann Pharmacother. Dec. 2007;41(12):1954-61. Epub Oct. 23, 2007.
Kent F. Burnett, C. Barr Taylor, and W. Stewart Agras; Ambulatory Computer-Assisted Therapy of Obesity: A New Frontier for Behavior Therapy; Journal of Consulting and Clinical Psychology, 1985, vol. 50, No. 5, 698-703; 1985 by the American Psychological Associates, Inc.
[No Author Listed], Metolose® Metolose® SR. ShinEtsu. 20 pages.
[No Author Listed], Carboxymethylcellulose (CMC). CMC Book. 1st edition. 28 pages.
[No Author Listed], CMC for Pharmaceutical Applications. Application Bulletin AB-94. 12 pages.
Sharma, V.K., et al., Oralpharmacokinetics of omeprazole and lansoprazole after single and repeated doses as intact capsules or as suspensions in sodium bicarbonate. Aliment Pharmacol Ther. Jul. 2000; 14(7): 887-92.
Sharma,V.K., Comparison of 24-hour intragastric pH using four liquid formulations of lansoprazole and omeprazole. Am J Health Syst Pharm. Dec. 1, 1999;56(23 Suppl 4):S18-21.
Chuong, M.C., et al., To Flavor or Not to Flavor Extemporaneous Omeprazole Liquid, International Journal of Pharmaceutical Compounding,Oct. 31, 2017, 21(6):500-512.
Extended European Search Report dated Feb. 1, 2020, for EP Application No. 17814171.9.
Extended European Search Report dated Feb. 2, 2020 for EP Application No. 17814171.9.
Non-Final Office Action dated Apr. 3, 2020 for U.S. Appl. No. 16/310,675.
XP-013157146, Process for preparing Posaconazole oral suspension, IP.com, Inc., West Henrietta, NY, US, May 8, 2013, ISSN: 1533-001.
Matthew, Mary et al., Stability of Omeprazole Solutions at Various pH Values as Determined by High Performance Liquid Chromatography, Drug Development and Industrial Pharmacy, (Year 1995).
International Search Report and Written Opinion dated Oct. 19, 2020, for PCT/US2020/042157.
Notice of Allowance dated Jun. 24, 2020 for U.S. Appl. No. 16/513,604.
Co-Pending U.S. Appl. No. 16/998,731, filed Aug. 20, 2020.
Co-Pending Track One U.S. Appl. No. 17/017,295, filed Sep. 10, 2020.

* cited by examiner

COMPOSITION AND METHOD FOR PROTON PUMP INHIBITOR SUSPENSION

RELATED APPLICATIONS

This application is a national stage filing under 35 U.S.C. § 371 of international application number PCT/US2017/037875, filed Jun. 16, 2017, which claims the benefit of priority under 35 U.S.C. § 119(e) to U.S. Provisional Application Ser. No. 62/351,271, filed on Jun. 16, 2016, entitled "COMPOSITION AND METHOD FOR PROTON PUMP INHIBITOR SUSPENSION" each of which is herein incorporated by reference in its entirety.

BACKGROUND OF THE INVENTION

Medications are often prescribed in a solid dosage form which many patients are unable to swallow, requiring these medications to be administered in an oral liquid form. The populations unable to swallow solid dosage forms and are in need of liquid formulations include pediatric patients, older patients with dysphagia, ICU patients and patients on enteral nutrition. Acid-related disorders are one of the most common conditions affecting these populations and as such are associated with significant healthcare resource utilization. Common disorders of acid-related conditions include: gastric ulcers, gastroesophageal reflux disease (GERD), *Helicobactor pylori* infection, non-ulcer related dyspepsia, gastritis and Zollinger-Ellison syndrome. The prevalence of chronic acid-related disorders in the US is on the rise, with GERD and peptic ulcer disease (PUD) responsible for the majority of occurrences. GERD is reported as afflicting more than 60 million Americans, showing 20% of the population having symptoms at least twice a week.

In order to successfully manage acid-related disorders, gastric acid production must be suppressed with the use of a Proton Pump inhibitor (PPI). PPIs are a critical group of medications that treat and prevent a range of diseases and pathologies that relate to the production of excess stomach acid and consequent damage to the GI tract. Several PPIs are approved for use, but are generally limited to solid dosage forms.

SUMMARY OF THE INVENTION

A stable liquid formulation of a compounded suspension of PPIs that is homogenous and stable for at least 30 days at refrigerated conditions is disclosed herein. Further disclosed is a diluent that can be used by a pharmacist to reconstitute a PPI powder to provide a liquid suspension suitable for ingestion that serves as the basis for a palatable, homogeneous, compounded preparation which allows for flexible dosing.

Disclosed herein are suspensions of proton pump inhibitors, as well as diluents (also known as carriers) for suspended PPI active pharmaceutical ingredients (API). These diluents or carriers or suspensions are liquid formulations intended for oral dosing or other delivery to the stomach or esophagus, and are variously described below as liquid formulations, liquids or formulations. These liquid formulations comprise a copolymer of ethylene oxide and propylene oxide, simethicone emulsion, a buffer system such as sodium bicarbonate and sodium citrate, as well as a preservative, a thickening agent, a sweetener, and water. In some embodiments, the formulations comprise a flavoring or sweetener that is not Ora-sweet.

In a particular embodiment, the copolymer of ethylene oxide and propylene oxide is Poloxamer 188. Poloxamers are also sold variously as Pluronics, Kolliphors or Symperonics. The use of a particular brand does not limit the scope of this invention, neither does the exact molecular weight designation of the poloxamer limit the scope of this invention. Those skilled in the art will recognize that other copolymers of ethylene oxide and propylene oxide, including poloxamers of similar but different structures and molecular weights can perform similar and substantially equivalent functions in various formulations that fall within the scope of this invention.

In certain specific embodiments, the thickening agents used in the liquid formulation of the invention are selected from the group consisting of xanthan gum and hydroxyethylcellulose. In some embodiments, hydroxyethylcellulose is a thickening agent and/or a suspending agent. In some embodiments, the formulation further comprises propylene glycol. One skilled in the art will recognize propylene glycol as an aid to properly disperse xanthan gum in the liquid formulation.

In further embodiments of the liquid formulation of the invention, the sweetening agents are selected from the group consisting of sorbitol, saccharin sodium, ammonium glycyrrhizate, and sucralose.

In a specific embodiment, the preservative is benzyl alcohol. In another specific embodiment, the liquid formulation comprises FD&C Red No. 40, Flavor Strawberry 28082, Saccharin Sodium, and Sucralose.

In certain embodiments, the pH of the liquid formulation is 8.0 or greater. In another embodiment, the pH of the liquid formulation is between 8.0 and 8.3, between 8.3 and 8.5, between 8.4 and 8.7, or between 8.7 and 9.0.

In one embodiment, the liquid formulations can be manufactured as taught by the invention to achieve a dynamic viscosity that is between 50 and 1000 centipoise (cP), between 30 and 50 cP, between 40 and 50 cP, between 50 and 100 cP, between 100-200 cP, between 200-300 cP, between 300-500 cP, between 500-700 cP, or between 700-1000 cP. In another embodiment, the liquid formulations can be manufactured as taught by the invention to achieve a dynamic viscosity that is between 200 and 300 centipoise. In a preferred embodiment, the liquid formulations can be manufactured as taught by the invention to achieve a dynamic viscosity that is between 40 and 50 centipoise (cP). In another preferred embodiment, the liquid formulations can be manufactured as taught by the invention to achieve a dynamic viscosity that is between 200 and 300 centipoise (cP). In yet another embodiment, the liquid formulations can be manufactured as taught by the invention to achieve a dynamic viscosity that is between 30 and 100 centipoise. In still another embodiment, the liquid formulations can be manufactured as taught by the invention to achieve a dynamic viscosity that is between 100 and 200 centipoise. In a further embodiment, the liquid formulations can be manufactured as taught by the invention to achieve a dynamic viscosity that is between 300 and 500 centipoise. One skilled in the art will appreciate that the methods and formulas disclosed herein can be adapted within the scope of what is pharmaceutically acceptable to provide a range of viscosities that permit the manufacture of liquid formulations for the dosing of PPI suspensions that can be adapted to further refine and optimize the balance of viscosity and suspendability.

The homogeneity and viscosity properties achieved with the formulations of the invention provide several advantages over prior art solutions. In some aspects, the formulations disclosed herein have improved homogeneity, resulting in an accurate uniform dose once resuspended. In some aspects, formulations of the invention retain homogeneity of less than +/−5% of assay for active pharmaceutical ingredient after at least 30 days. In another aspect of the invention, the viscosity of the liquid formulations is optimized by adding Poloxamer 188. In yet another aspect of the invention, the liquid formulations are optimized by reducing the suspending agent to eliminate agglomeration. Agglomeration—if present—can lead to a non-uniform suspension. Extraordinarily high viscosities may cause residual volumes in the container or delivery device upon dispensing, which may lead to noncompliance caused by incomplete dosing resulting from short fills.

In a specific embodiment, the formulations disclosed by the invention may be used to create a suspension of PPI wherein the percent of active pharmaceutical ingredient dissolved is consistently greater than 95% by dissolution assay after a transfer time of 1 minute, 3 minutes, 5 minutes, or 10 minutes. This dissolution of the formulations of the invention is quite surprising and beneficial. The rate and quantity of dissolution is important to the accuracy of the dose delivered to a patient. The dissolution properties that are achieved with the formulations of the invention provide several advantages over prior art solutions.

One embodiment of the liquid formulations as taught by the invention comprises Benzyl Alcohol, FD&C Red No. 40, Flavor Strawberry 28082, Ammonium Glycyrrhizate, Poloxamer 188, Simethicone, Sodium Bicarbonate, Sodium Citrate, Sucralose, and Water.

In a specific embodiment a liquid formulation of the invention comprises:
a. 0.4%-0.6% (w/v) Benzyl Alcohol, NF;
b. 0.002%-0.005% (w/v) FD&C Red No. 40;
c. 0.1%-0.2% (w/v) Flavor Strawberry 28082;
d. 0.06%-0.08% (w/v) Ammonium Glycyrrhizate, NF;
e. 1.0%-3.0% (w/v) Poloxamer 188, NF;
f. 0.1%-0.3% (w/v) Simethicone Emulsion, USP (30%);
g. 8.0%-8.8% (w/v) Sodium Bicarbonate, USP, Granular No. 5;
h. 0.5%-1.5% (w/v) Sodium Citrate, USP (Dihydrate);
i. 0.35%-0.5% (w/v) Sucralose, NF;
j. Purified water, USP.

In another specific embodiment a liquid formulation of the invention comprises:
a. 0.5% (w/v) Benzyl Alcohol, NF;
b. 0.003% (w/v) FD&C Red No. 40;
c. 0.15% (w/v) Flavor Strawberry 28082;
d. 0.07% (w/v) Ammonium Glycyrrhizate, NF;
e. 2.0% (w/v) Poloxamer 188, NF;
f. 0.2% (w/v) Simethicone Emulsion, USP (30%);
g. 8.4% (w/v) Sodium Bicarbonate, USP, Granular No. 5;
h. 1.0% (w/v) Sodium Citrate, USP (Dihydrate);
i. about 0.4% (w/v) Sucralose, NF; and
j. Purified water, USP.

In another aspect of the invention a liquid formulation is provided and comprises:
0.4%-0.6% (w/v) Benzyl Alcohol, NF;
0.2%-0.5% (w/v) hydroyethylcellulose;
1.0%-6.0% (w/v) Poloxamer 188, NF;
0.1%-0.3% (w/v) Simethicone Emulsion, USP (30%);
8.0%-8.8% (w/v) Sodium Bicarbonate, USP, Granular No. 5;
0.5%-1.5% (w/v) Sodium Citrate, USP (Dihydrate);
0.35%-0.5% (w/v) Sucralose, NF;
1.5%-4% (w/v) Sorbitol solution
8%-12% (w/v) Glycerin 99.7%

In a specific embodiment a liquid formulation of the invention comprises:
0.4%-0.6% (w/v) Benzyl Alcohol, NF;
0.002%-0.005% (w/v) FD&C Red No. 40;
0.1%-0.2% (w/v) Flavor Strawberry 28082;
0.2%-0.5% (w/v) hydroyethylcellulose;
1.0%-6.0% (w/v) Poloxamer 188, NF;
0.1%-0.3% (w/v) Simethicone Emulsion, USP (30%);
8.0%-8.8% (w/v) Sodium Bicarbonate, USP, Granular No. 5;
0.5%-1.5% (w/v) Sodium Citrate, USP (Dihydrate);
0.35%-0.5% (w/v) Sucralose, NF;
Purified water, USP
1.5%-4% (w/v) Sorbitol solution
8%-12% (w/v) Glycerin 99.7%

In a specific embodiment a liquid formulation of the invention comprises:
0.5% (w/v) Benzyl Alcohol, NF;
0.003% (w/v) FD&C Red No. 40;
0.15% (w/v) Flavor Strawberry 28082;
0.35% (w/v) hydroyethylcellulose;
2.0% (w/v) Poloxamer 188, NF;
0.15% (w/v) Simethicone Emulsion, USP (30%);
8.4% (w/v) Sodium Bicarbonate, USP, Granular No. 5;
1.0% (w/v) Sodium Citrate, USP (Dihydrate);
0.4% (w/v) Sucralose, NF;
Purified water, USP
2.5% (w/v) Sorbitol solution
10% (w/v) Glycerin 99.7%

In a specific embodiment a liquid formulation of the invention comprises:
0.5% (w/v) Benzyl Alcohol, NF;
0.003% (w/v) FD&C Red No. 40;
0.15% (w/v) Flavor Strawberry 28082;
0.35% (w/v) hydroyethylcellulose;
4.0% (w/v) Poloxamer 188, NF;
0.15% (w/v) Simethicone Emulsion, USP (30%);
8.4% (w/v) Sodium Bicarbonate, USP, Granular No. 5;
1.0% (w/v) Sodium Citrate, USP (Dihydrate);
0.4% (w/v) Sucralose, NF;
Purified water, USP
2.5% (w/v) Sorbitol solution
10% (w/v) Glycerin 99.7%

In one aspect, the suspension or diluent of the invention comprises:
0.5% (w/v) Benzyl Alcohol, NF;
0.003% (w/v) FD&C Red No. 40;
0.15% (w/v) Flavor Strawberry 28082;
0.07% (w/v) Ammonium Glycyrrhizate, NF;
2.00% (w/v) Poloxamer 188, NF;
5.0% (w/v) Propylene Glycol, USP;
0.2% (w/v) Simethicone Emulsion, USP (30%);
8.4% (w/v) Sodium Bicarbonate, USP, Granular No. 5;
1.0% (w/v) Sodium Citrate, USP (Dihydrate);
0.45% (w/v) Sucralose, NF;
0.4% (w/v) Xanthan Gum, NF; and
Purified water, USP.

In another aspect of the disclosed invention, the suspension or diluent comprises:
0.5% (w/v) Benzyl Alcohol, NF;
0.003% (w/v) FD&C Red No. 40;
0.15% (w/v) Flavor Strawberry 28082;
0.07% (w/v) Ammonium Glycyrrhizate, NF;
0.25% (w/v) Hydroxyethyl cellulose, NF;
2.0% (w/v) Poloxamer 188, USP;
0.08% (w/v) Saccharin Sodium, USP;
0.2% (w/v) Simethicone Emulsion, USP (30%);

8.4% (w/v) Sodium Bicarbonate, USP, Granular No. 5;
1.0% (w/v) Sodium Citrate, USP (Dihydrate);
2.5% (w/v) Sorbitol Solution, USP (70%);
0.4% (w/v) Sucralose, NF; and
Purified water, USP.

Another embodiment of the present invention is a liquid diluent comprising: 0.4-0.6% (w/v) Benzyl Alcohol, NF; 0.002-0.005% (w/v) dye; 0.1-0.2% (w/v) flavoring; 0.06-0.08% (w/v) Ammonium Glycyrrhizate, NF; 1.00-3.00% (w/v) Poloxamer 188, NF; 4.0-6.0% (w/v) Propylene Glycol, USP; 0.1-0.3% (w/v) Simethicone Emulsion, USP; 8.0-8.8% (w/v) Sodium Bicarbonate, USP; 0.5-1.5% (w/v) Sodium Citrate, USP (Dihydrate); 0.4-0.45% (w/v) Sucralose, NF; 0.3-0.5% (w/v) Xanthan Gum, NF; and purified water, USP.

A preferred embodiment of the present invention is a liquid diluent comprising: 0.5% (w/v) Benzyl Alcohol, NF; 0.003% (w/v) FD&C Red No. 40; 0.15% (w/v) Flavor Strawberry 28082; 0.07% (w/v) Ammonium Glycyrrhizate, NF; 2.00% (w/v) Poloxamer 188, NF; 5.0% (w/v) Propylene Glycol, USP; 0.2% (w/v) Simethicone Emulsion, USP (30%); 8.4% (w/v) Sodium Bicarbonate, USP, Granular No. 5; 1.0% (w/v) Sodium Citrate, USP (Dihydrate); 0.45% (w/v) Sucralose, NF; 0.4% (w/v) Xanthan Gum, NF; and Purified water, USP.

Another preferred embodiment of the present invention is a liquid diluent comprising: 0.4-0.6% (w/v) Benzyl Alcohol, NF; 0.002-0.005% (w/v) dye; 0.1-0.2% (w/v) flavoring; 0.06-0.08% (w/v) Ammonium Glycyrrhizate, NF; 0.2-0.3% (w/v) Hydroxyethylcellulose, NF; 1.00-3.00% (w/v) Poloxamer 188, NF; 0.07-0.09% (w/v) Saccharin Sodium, USP; 0.1-0.3% (w/v) Simethicone Emulsion, USP; 8.0-8.8% (w/v) Sodium Bicarbonate, USP; 0.5-1.5% (w/v) Sodium Citrate, USP (Dihydrate); 2.0-3.0% (w/v) Sorbitol Solution, USP (70%); 0.3-0.5% (w/v) Sucralose, NF; and purified water, USP.

An additional preferred embodiment is a liquid diluent comprising: 0.5% (w/v) Benzyl Alcohol, NF; 0.003% (w/v) FD&C Red No. 40; 0.15% (w/v) Flavor Strawberry 28082; 0.07% (w/v) Ammonium Glycyrrhizate, NF; 0.25% (w/v) Hydroxyethylcellulose, NF; 2.00% (w/v) Poloxamer 188, NF; 0.08% (w/v) Saccharin Sodium, USP; 0.2% (w/v) Simethicone Emulsion, USP (30%); 8.4% (w/v) Sodium Bicarbonate, USP, Granular No. 5; 1.0% (w/v) Sodium Citrate, USP (Dihydrate); 2.5% (w/v) Sorbitol Solution, USP (70%); 0.4% (w/v) Sucralose, NF; and Purified water, USP.

A specific embodiment of the invention is that the liquid formulations taught can be used in a method that delivers a PPI suspension to a subject, comprising passing the PPI suspension through a tube. In some embodiments, the tube is a nasogastric tube. In some embodiments, the tube can be any suitable diameter. In some embodiments, the tube has a diameter of between 5 and 12 French. Non-limiting examples include a tube with a diameter of 5 French, 8 French, 10 French, or 12 French. In one embodiment, the liquid formulation can be used in a method that delivers a PPI suspension to a subject, comprising passing the PPI suspension through a tube having a minimum diameter of 5 French at a rate of 9 ml/min without tube occlusion. In some aspects of the present invention, post tube administration presents little to no PPI residue in the tube, suggesting the patient will receive a complete dose. Formulations of the present invention may be delivered to pediatric patients through a tube having a very narrow diameter, for example having a maximum diameter of 5 French or 8 French.

The invention disclosed includes a suspension of a proton pump inhibitor (PPI) comprising a PPI, a copolymer of ethylene oxide and propylene oxide; simethicone emulsion; Sodium Bicarbonate; and Sodium Citrate, USP (Dihydrate). In some aspects, the suspension is stable for at least 30 days when stored at 2-8 degrees Celsius. In another aspect of the invention, the diluent is stable for at least 24 months when stored between 2 and 8 degrees Celsius. In another aspect of the invention, the diluent is stable for at least 24 months when stored between 2 and 15 degrees Celsius. In yet another aspect of the invention, the diluent is stable for at least 24 months when stored between 2 and 25 degrees Celsius.

Also disclosed are stable homogenous suspension of a proton pump inhibitor (PPI) having a dynamic viscosity of 200 to 300 centipoise (cP).

Suspensions and diluents disclosed herein, in some aspects, have a pH of at least 8.0. In addition, suspensions disclosed herein, in some aspects, retain homogeneity of less than +/−5% of assay for active pharmaceutical ingredient after at least 30 days. In yet another aspect of the invention, suspensions disclosed herein maintain homogeneity of the active pharmaceutical ingredient for at least 30 days after reconstitution.

Each of the embodiments of the invention can encompass various recitations made herein. It is, therefore, anticipated that each of the recitations of the invention involving any one element or combinations of elements can, optionally, be included in each aspect of the invention.

DETAILED DESCRIPTION

The invention encompasses liquid compounded formulations of proton pump inhibitors as well as related compounding kits. The liquid formulations have enhanced stability for 30 days at refrigerated conditions with respect to other available liquid formulations. As is well known in the art, compounded formulations include reconstituted formulations which are stable for up to 14 days.

Also provided herein are methods of treating acid related disorders comprising administering to a patient, such as a child or an elderly patient an oral liquid formulation compounded from PPI powder.

Commonly, pediatric and geriatric populations encounter difficulty being administered solid oral dosage forms such as capsules and tablets which may lead to noncompliance with the recommended pharmacotherapy with the solid oral dosage forms and likely results in rendering the therapy ineffective. Solid oral dosage forms are usually not favorable for pediatric and geriatric populations due to the potential risk of choking. Additionally, certain solid oral dosage forms of medications cannot be administered simply by crushing (e.g., patients requiring various types of feeding tubes) because of the coating or drug delivery mechanism by which the drug is released. For most community pharmacies (retail/chain and independent), extemporaneously compounded PPIs do not provide the ease of use, flavoring, flexible dosing, or a uniform formulation.

The current method of overcoming the aforementioned drawbacks of the solid oral dosage form of PPIs is emptying multiple capsules and dissolving the granules in sodium bicarbonate to achieve the prescribed concentration. This method of preparation is cumbersome and time-consuming for pharmacists in today's busy pharmacies. Another commonly compounded preparation is Zegerid powder for oral solution packet which is easily reconstituted in water, but doesn't allow for flexible dosing.

The liquid formulations of the invention has 30 day stability at refrigerated storage conditions. The liquid formulations of the invention have improved palatability compared to commercially available formulations, and when compared to previously described oral formulations or compounded formulations. The liquid formulations of the invention have improved homogeneity when compared to commercially available liquid formulations. The liquid formulations of the invention has optimized viscosity to reduce agglomeration and adherence of the product to the container.

Proton pump inhibitors (PPIs) are medicines that work by reducing the amount of stomach acid made by glands in the lining of the stomach. PPIs are used to relieve symptoms of acid reflux or gastroesophageal reflux disease (GERD), a condition in which food or liquid moves up from the stomach to the esophagus. PPIs can be used to treat a peptic or stomach ulcer, and to treat damage to the lower esophagus caused by acid reflux. PPIs can be used to treat a variety of other diseases characterized by excessive acid secretion in the stomach, and can also be used prophylactically to manage the risk of ulceration and upper gastrointestinal tract bleeding in critical care patients. PPIs are among the most widely sold drugs in the world, and one of them, omeprazole, is on the World Health Organization's List of Essential Medicines.

There are many types (and brands) of PPIs, including Omeprazole (Prilosec), Esomeprazole (Nexium), Lansoprazole (Prevacid), Rabeprazole (AcipHex), Pantoprazole (Protonix), and Dexlansoprazole (Dexilant), all of which are available in capsule format. Some PPIs are formulated for extended release while others are formulated for immediate release. Zegerid (omeprazole with sodium bicarbonate) is formulated for immediate release and available as a capsule and a powder. PPIs are taken by mouth. Commonly, PPIs are taken without food, 30 minutes or more prior to the first meal of the day.

Due to the lack of alternative formulations, PPIs have been of limited use in patients who are incapable of, or have difficulty, swallowing capsules or tablets. Most PPIs are available only as enteric coated granules contained in a gelatin capsule. After dissolution of the gelatin capsule in the stomach acid, the enteric coating protects the granules from dissolution during passage through the stomach until they reach the small intestine where absorption occurs. Subsequently, one PPI, omeprazole, has become commercially available in an alternate formulation that includes omeprazole (active ingredient) with sodium biocarbonate (to protect the active ingredient from stomach acid during passage to the small intestine). This drug, known as Zegerid, may only be administered with water and, once dissolved in water from the dry powder, is supposed to be consumed immediately. Other formulations containing PPI active ingredients are currently not available in a liquid form or are reconstitutable as a liquid.

The liquid formulations of the current invention are more palatable than Zegerid suspension and extemporaneously compounded PPIs and have enhanced stability at refrigerated conditions, ideal viscosity and significantly improved homogeneity properties. In addition, the disclosed formulations may be used to stabilize and dose PPIs other than omeprazole and lansoprazole. Non-limiting examples of the PPIs that the disclosed formulations may be used to stabilize and dose include lansoprazole, dexlansoprazole, esomeprazole, rabeprazole, and ilaprazole. In addition, as PPIs are typically dosed daily, the liquid formulations of the current invention allow a compounding pharmacy to prepare doses for many days at a consistent concentration in a convenient presentation that provides reliable delivery of API per unit dose. This provides enhanced compliance in patients over the alternate methods of making daily doses from powder packets which, in contrast, does not allow for flexible dosing. Zegerid, the only PPI currently available commercially as a powder for liquid dosing is labeled as requiring immediate consumption after reconstitution in water. Zegerid also lacks features of the current invention, such as improving the taste of the dose, while other PPI active molecules are commercially unavailable in any liquid dosage form.

A major advantage of the invention is the flexibility of dose that can be prescribed by the physician. The ability to reconstitute a supply of PPI in a liquid formulation to be dosed orally to a patient later in the day, over the course of several days, over the course of a week, or over the course of several weeks, provides ease of use to the compounding pharmacist, physician, and patient. This provides a time saving and cost effective method of producing multiple drug doses in the pharmacy for a single patient. In addition, as the method described utilized bulk API rather than recycling final dosage forms of licensed drug products (i.e. recovering granules of drug from drug capsules) the invention provides additional consistency over alternative compounding formulation methods. In some embodiments, the formulations described and the preparation methods disclosed have been shown to produce comparably stable and homogenous liquid formulations from more than one source of bulk API, demonstrating the broad applicability of the methods disclosed.

The ability to deliver a single container of liquid drug to the patient provided by the present invention also solves several problems posed by existing dose formats to patients. In addition, the ability to reliably deliver the dose in patients who cannot swallow capsules or who have difficulty doing so, the present invention also avoids the complexity to the patient of having to reconstitute and then immediately drink the only available PPI that is provided for liquid formulation. This provides additional benefit to the patient in terms of increased compliance and reduction in errors in reconstitution.

The ability to use the liquid formulations of the invention also offers advantages to physicians, as it provides the ability to prescribe with more flexibility for a range of challenging and otherwise vulnerable patients. In addition, by utilizing the formulations of the present invention, the physician is able to prescribe doses of other PPIs in a format that assures the safe and reliable delivery of drug to patients in a palatable, stable, and homogenous format that can be prepared in a pharmacy, thus minimizing errors of preparation by patients. The palatability of the disclosed formulations improves patient compliance and minimizes patient distress. The liquid nature of the formulations disclosed allows the dosing of PPIs to children who are unable to reliably swallow capsules. In addition, the liquid nature of the formulations disclosed allows the dosing of PPIs to elderly patients who are unable to reliably swallow capsules. Furthermore, the liquid nature of the formulations disclosed allows the dosing of PPIs to critical care patients who are otherwise unable to swallow capsules due to intubation or other injuries, pathologies, or interventions that inhibit the ability to receive or take medication in solid format. In addition, the ability of the invention to have a lower viscosity of the formulations in the pharmacy provides a means to improve the delivery of the drug by nasogastric feeding tube or other device designed, intended, or used to deliver liquids to a patient's stomach or esophagus.

The liquid formulations disclosed provide a vehicle for the delivery of a suspension of PPI API within a solution comprising a copolymer of ethylene oxide and propylene oxide, simethicone emulsion, a buffer system (for example sodium bicarbonate and sodium citrate) a preservative, a thickening agent, a sweetener, and water. While not excluding the possibility that other ingredients contribute to the stability of the formulation, the copolymer of ethylene oxide and propylene oxide is included to stabilize the active ingredient. Similarly, the use of simethecone contributes to stability by minimizing the formation of foam on mixing or agitation during formulation, or incidentally during transport, use, and storage. The formation of foam could be associated with conditions denaturing the API or conditions that would diminish the patient's ability to measure an exact dose. Sodium bicarbonate and sodium citrate serve to provide a buffered solution that promotes the maintenance of a constant pH during liquid storage after formulation, and that promotes the neutralization of stomach acid after dosing in order to minimize the acid digestion or degradation of the API in the patient's stomach. Thickening agents and sweeteners are included to improve the handling, appearance, and palatability of the finished dosage.

While sodium citrate and sodium bicarbonate are the buffers used in one embodiment, this is a non limiting example of the buffers that can be used in the present invention. Other buffers include pharmacologically acceptable combinations of cations selected from sodium, potassium, magnesium, calcium, and aluminum and anions selected from bicarbonate, hydroxide, gluconate, glycinate, and other appropriate amino acid salts. Additional buffering agents can include other forms of citrate, tartrates, acetates, carbonates, phosphates, metaphosphates, glycerophosphates, polyphosphates, pyrophosphates, and certain oxides in pharmacologically and pharmaceutically acceptable combinations of anions and cations providing buffering capacity as known in the art.

Preservatives added include anti-microbials, anti-oxidants, and agents providing biocidal or biostatic activity, such that a low bioburden is maintained in the formulation of the invention from preparation through storage, and during routine use by patients and clinicians. Exemplary preservatives include benzyl alcohol or other pharmaceutically acceptable alcohol, ascorbic acid, ascrobyl palmitate or other pharmaceutically acceptable ascorbate salts, BHA, BHT, citric acid or other citrate salts, sodium benzoate, benzoic acid or other pharmaceutically acceptable benzoate salts, sodium bisulfate, sodium metabisulfite, sodium sulfite, parabens, potassium sorbate or other pharmaceutically acceptable sorbate salts, or vanillin.

Sweeteners or sweetening agents may include any compounds that provide a sweet taste to enhance the palatability of the formulation, including natural and synthetic sugars and natural and synthetic sweeteners (i.e., non-sugar sweetening agents). These could include glucose, fructose, sucrose, or other pharmaceutically acceptable monosaccharide and disaccharides or sugar alcohols, such as xylitol. Also, sweeteners may include maltodextrin, polydextrose and the like. Other sweeteners may include glycerin, inulin, maltol, salts of acesulfame, alitame, aspartame, neotame, cyclamate salts, saccharin and its salts, and other artificial and naturally-occurring agents providing sweetness either singly or in combination.

In other embodiments, the liquid formulations comprise a flavoring agent or flavorant to enhance the flavor or aroma of the dose, and to improve general palatability of the dose, thus helping to mask the flavor of the PPI active ingredient which patients may find unpleasant. This provides an improved experience for patients, and better compliance with the drug regimen desired by clinicians. Suitable natural or artificial flavors can be selected from pharmaceutically acceptable options as described in standard pharmacy references which are known to those skilled in the art. In a particular embodiment, strawberry flavor is used. The use of strawberry flavor has been found to be effective in helping to mask the unpleasant flavor of omeprazole. In other embodiments, other pharmaceutically acceptable flavors can be used to mask the flavor of other ingredients, for example other PPI APIs, and to enhance palatability and thus compliance in a range of patient populations. Natural and synthetic flavors can be used and adapted to the palate of diverse patient populations, including but not limited to, age- and culturally-related flavor preferences (for example bubble gum flavor for pediatric patients).

In further embodiments, the liquid formulation may contain a pharmaceutically acceptable coloring agent. Many such agents are approved for use by the U.S. Food and Drug Administration, and are well known to those skilled in the art of compounding pharmacy. The use of color can enhance the aesthetic appearance of the dose as well as providing confirmation of the identity of the drug in a context where more than one oral formulation is being prepared, stored, transported, or used. Enhancing the aesthetic appearance of the dose increased the overall palatability of the dose, which provides benefits to patients and clinicians in terms of improved patient experience and improved compliance with the drug regimen. The ability to unambiguously identify the medication in the pharmacy, clinical, and patient context provides benefits to the patient by reducing the scope for errors in the preparation, storage, handling, transport, and use of the medication. In addition, the use of color in the formulations can mask color changes in the formulation lacking additional color agents. For example, uncolored formulations may change color due to chemical changes taking place during storage that do not affect the safety, potency, or efficacy of the medication, but that might confuse a patient or clinician, or that might lead to a lack of compliance with a prescribed drug regimen.

A key problem in devising oral liquid formulations that are practical, safe, and effective to make and use, is the balance required between palatability and the handling requirements of the dose form on the one hand, and the stability of the formulation and the homogeneity of the doses on the other. Where, as in the present invention, it is desired to produce a liquid medication for oral delivery in a series of doses spread over time, it is critical to provide a formulation in which the potency of the API remains acceptably constant over the time that the formulation is to be used, so that from the first dose to last dose the same dose of active drug is delivered per unit volume of the formulation dosed to the patient. In addition, as in the case of the present invention where the API is presented as a suspension in a liquid formulation, it is necessary that the formulation is capable of providing homogenous doses. That is, that the API does not clump, settle to the bottom, float to the top, or stick to the sides of the container or any dosing or manufacturing device in a manner that would cause the dose of API contained in unit volume doses obtained from the preparation to vary unacceptably. It is generally desirable for the formulation to be sufficiently pleasant for the patient to consume and assure compliance with the regimen prescribed by the clinician, where the dose is delivered orally. It is generally desirable for the viscosity of the liquid formulation to be low enough to facilitate handling of the formulation in the manufacture, storage, and dosing in a manner such that there are not unacceptable losses of drug, i.e., material adhering to the containers or equipment used for manufacture and storage or by adherence or clumping within the drug delivery device such as a nasogastric feeding tube. If too much drug adheres to and clumps on equipment and containers used to make, store, and deliver doses, then the delivery of API to the patient becomes unreliable, which undermines the consistency, efficacy, and safety of therapy.

However, if the liquid suspension used is insufficiently viscous, then settling may occur during manufacture, storage or use and will impact the homogeneity of the doses. In general, a thick and viscous solution will provide a more reliable medium in which a suspended API can maintain homogenous distribution within the prepared formulation. The formulations of the present invention resolve homogeneity concerns by providing a balance of viscosity in the formulation that provide levels of viscosity that are acceptable to patients and clinicians for dosing orally and by nasogastric tube (or similar devices), while maintaining stability and homogeneity over its shelf life at refrigerated conditions. In a particular embodiment, a PPI oral formulation with viscosity between 50 and 1000 cP (centipoise) showed homogenous recovery of API throughout the formulated container after initial preparation and after 2 days, after 15 days, and after 30 days when stored refrigerated. In each case, samples taken from the top, middle and bottom of the container were shown to contain the expected and desired dose of API, and no samples were seen that were either subpotent or superpotent with respect to the dose of the API. Equivalent results were obtained from two different sources of the PPIs. Comparable results were obtained for all API sources with homogenous doses seen throughout the container initially and after 30 days refrigeration.

In an additional embodiment, an alternate formulation of the invention was compounded to a viscosity between 40 and 50 cP using both sources of API as described above. This lower viscosity solution also showed that the initial doses of API were recovered at close to 100% of the nominal formulation value throughout the container as formulated. Subsequent doses withdrawn from the container after 2, 15 and 30 days of refrigerated storage showed stable and homogenous doses of API at each timepoint and throughout the container. Each dose containing a pharmaceutically acceptable dose of API with no superpotent doses and no subpotent doses recovered, where the container was sampled at the top, middle and bottom.

Refrigerated temperature, also as defined by the USP, is between 2 and 8 degrees Celsius, and is sometimes designated by the nominal value of 5 degrees Celsius. In each case, the formulations of the invention that were shown to be stable showed acceptable recovery of the expected API from the dose where acceptable is >95% or alternately >90% of the nominal or starting dose of API, as well as maintaining acceptably constant pH and acceptably constant acid neutralization potential.

Specific examples are provided below of pharmaceutically acceptable formulations that achieve appropriate homogeneity and stability in useful, practical and palatable presentations. However, one skilled in the art will appreciate that the methods and formula disclosed can be adapted within the scope of what is pharmaceutically acceptable to provide a range of viscosities that permit the manufacture of liquid formulations for the dosing of PPI suspensions that can be adapted to further refine and optimize the balance of viscosity and suspendability. This balance allows the customization of formulations to allow increased use of suspending agents to increase time-in-suspension, and thus sustaining homogeneity of the preparation over the intended use life.

The need to achieve a balance as noted above is driven by the effective upper limit on viscosity, which depends on a number of factors, which includes, but is not limited to, problems with agglomeration, homogeneity, managing palatability, and managing the usability of the formulations in specific dosing scenarios. A useful formulation cannot be so viscous as to create difficulty in manufacture, transfer to the storage container, transfer to the dosing container, and transfer to the patient. Where a formulation is too viscous, unacceptable loss of product may occur at one of the steps leading to inconsistent or unreliable delivery of doses. An additional problem created by excessive viscosity is that it may render the formulation unpalatable to the patient which may decrease compliance with the desired drug regimen. Another problem created by excessive viscosity is the inability to deliver the dose through a feeding tube or similar device. It is within the scope of the invention that one skilled in the art will be able to adapt the teaching contained herein and the specific examples given below to create a suspension that balance the concerns outlined here to achieve safe, efficacious and practical formulations for the delivery of suspended PPIs.

The invention also encompasses and contemplates compounding kits used to prepare the formulations, including but not limited to, approved drug formulations for reconstitution.

Unless defined otherwise, all technical and scientific terms used herein have the same meanings as commonly understood by one skilled in the art. Although any methods and materials similar or equivalent to those described herein can be used in the practice of testing of embodiments described herein, certain preferred methods, devices, and materials are now described.

As used herein and in the appended claims, the singular forms "a", "an", and "the" include plural reference unless the context clearly dictates otherwise. Thus, for example, reference to "an excipient" is a reference to one or more excipients and equivalents thereof known to those skilled in the art, and so forth.

The term "about" is used to indicate that a value includes the standard level of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or". The terms "comprise", "have", and "include" are open-ended linking verbs. Any forms or tenses of one or more of these verbs "comprises," "comprising," "has," "having," "includes," and "including" are also open-ended. For example, any method that "comprises," "has" or "includes" one or more steps is not limited to possessing only those one or more steps and also covers other unlisted steps.

"Optional" or "optionally" may be taken to mean that the subsequently described structure, event or circumstance may or may not occur, and that the description includes instances where the events occurs and instances where it does not.

As used herein, the term "therapeutic" means an agent utilized to treat, combat, ameliorate, prevent or improve an unwanted condition or disease of a patient. In some embodiments, a therapeutic agent is directed to the reduction of the production of gastric acid, and in certain embodiments the therapeutic is a proton pump inhibitor, and in specific embodiments the proton pump inhibitor is omeprazole or lansoprazole. In certain embodiments the therapeutic can be used in the treatment of one or more conditions including dyspepsia, peptic ulcer disease, duodenal ulcer, gastric ulcer, *Helicobacter pylori*, gastroesophageal reflux disease, laryngopharyngeal reflux causing laryngitis, Barrett's esophagus, erosive esophagitis, eosinophilic esophagitis and stress gastritis. In other embodiments the therapeutic could be used for prevention of ulcer and/or upper gastrointestinal tract bleeding for critical care patients. In other embodiments, the therapeutic could be used to treat conditions that cause hypersecretion of stomach acid such as Zollinger-Ellison syndrome or gastrinomas.

As used herein, the terms "patient," "subject" and "individual" are intended to include living organisms in which certain conditions as described herein can occur. Examples include humans, monkeys, cows, sheep, goats, dogs, cats, mice, rats, and transgenic species thereof. In a preferred embodiment, the patient is a primate. In certain embodiments, the primate or subject is a human. In certain instances, the human is an adult. In certain instances, the human is a child. In certain instances, the human is elderly. Other examples of subjects include experimental animals such as mice, rats, dogs, cats, goats, sheep, pigs, and cows.

By "pharmaceutically acceptable", it is meant the carrier, diluent or excipient must be compatible with the other ingredients of the formulation and not deleterious to the recipient thereof.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

A "therapeutically effective amount" or "effective amount" as used herein refers to the amount of active compound or pharmaceutical agent that elicits a biological or medicinal response in a tissue, system, animal, individual or human that is being sought by a researcher, veterinarian, medical doctor or other clinician, which includes one or more of the following: (1) preventing the disease; for example, preventing a disease, condition or disorder in an individual that may be predisposed to the disease, condition or disorder but does not yet experience or display the pathology or symptomatology of the disease, (2) inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) ameliorating the disease; for example, ameliorating a disease, condition or disorder in an individual that is experiencing or displaying the pathology or symptomatology of the disease, condition or disorder (i.e., reversing the pathology and/or symptomatology). As such, a non-limiting example of a "therapeutically effective amount" or "effective amount" of a composition of the present disclosure may be used to inhibit, block, or reverse the activation of gastric acid secretion.

The terms "treat," "treated," "treatment," or "treating" as used herein refers to both therapeutic treatment in some embodiments and prophylactic or preventative measures in other embodiments, wherein the object is to prevent or slow (lessen) an undesired physiological condition, disorder or disease, or to obtain beneficial or desired clinical results. For the purposes described herein, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. A prophylactic benefit of treatment includes prevention of a condition, retarding the progress of a condition, stabilization of a condition, or decreasing the likelihood of occurrence of a condition. As used herein, "treat," "treated," "treatment," or "treating" includes prophylaxis in some embodiments.

Various aspects of the embodiments described above may be used alone, in combination, or in a variety of arrangements not specifically discussed in the embodiments described in the foregoing, and is therefore not limited in its application to the details and arrangement of components set forth in the foregoing description or illustrated in the drawings. For example, aspects described in one embodiment may be combined in any manner with aspects described in other embodiments.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Example 1

An exemplary formulation of a liquid diluent of the present invention was prepared. In order to make a relative high viscosity formulation with approximately 50-1000 cP viscosity in a preparation at batch size of 2 liters, the following method was successfully used. For reference purposes, this formulation is referenced herein as Formula C0092

1. 1700 mL of purified water, USP was added to a suitable container.
2. 168 grams of sodium bicarbonate, USP (Granular No. 5) was added while mixing the preparation.
3. 20.0 grams of sodium citrate, USP (dihydrate) was added to the preparation while continuing to mix,
4. 9.0 grams of sucralose, NF was added to the preparation while continuing to mix.
5. 1.4 grams of ammonium glycyrrhizate, NF (also known as Magnasweet 100) was added to the preparation while continuing to mix.
6. 40 grams of Poloxamer 188, NF was added to the preparation while continuing to mix.
7. Mixing was continued for 30 to 45 minutes.
8. Preparation of Premix 1: 100 grams of propylene glycol, USP was added to a suitable container
9. 8.0 grams of xanthan gum, NF was added to the container and mixed using a suitable spatula until completely dispersed and no lumps were present. End of Premix 1

10. After the mixing at Step 7 was complete, while maintaining continuous mixing Premix 1 was added to the main container and the contents of the main container were mixed for an additional 30 to 45 minutes.
11. Preparation of Premix 2: About 5 mL of purified water, USP was added to a suitable container. To this container 60 mg of FD&C Red No. 40 was added and mixed using a suitable spatula until all contents were completely dissolved. End of Premix 2.
12. When the mixing of step 10 was completed, Premix 2 was added under continuous mixing to the main container.
13. 10.0 grams of benzyl alcohol, NF was slowly added while mixing.
14. 3.0 grams of strawberry flavor 28082 (CW08) was added while mixing.
15. 4.0 grams of simethicone emulsion, USP (30%) was added while mixing.
16. The solution was mixed for 10-15 minutes.
17. sufficient purified water, USP was added to make the final volume up to 2000 mL
18. The solution was mixed for a further 10-15 minutes.
19. The batch was transferred to containers using bottle B325-38-BLA-WHT and cap 8040-A.

Example 2

Another exemplary formulation of a liquid diluent of the present invention was prepared. In order to make a relative low viscosity formulation with approximately 40-50 cP viscosity in a preparation at batch size of 2 liters, the following method was successfully used. For reference purposes, this formulation is referenced herein as Formula C0093.

1. 1700 mL of purified water, USP was added to a container.
2. 168 grams of sodium bicarbonate, USP (Granular No. 5) was added while mixing.
3. 1.60 grams of saccharin sodium, USP was added while mixing.
4. 20.0 grams of sodium citrate, USP (dihydrate) was added while mixing.
5. 8.0 grams of sucralose, NF was added while mixing.
6. 1.4 grams of ammonium glycyrrhizate, NF (also known as Magnasweet 100) was added while mixing
7. 40 grams of Poloxamer 188, NF was added while mixing.
8. Mixing was continued for 30 to 45 minutes.
9. Preparation of Premix 1: To a suitable container 50.0 grams of sorbitol solution, USP (70%) was added.
10. 5.0 grams of hydroxyethylcellulose, NF (also known as Natrosol 250HHX) was added while mixing using a suitable spatula until completely dispersed and no lumps were present. End of Premix 1
11. After the mixing at Step 8 was complete, while maintaining continuous mixing the Premix 1 was added to the main container and continued to mix the contents of the main container for an additional 30 to 45 minutes.
12. 10.0 grams of benzyl alcohol, NF was slowly added while mixing.
13. 4.0 grams of simethicone emulsion, USP (30%) was added while mixing.
14. Mixing was continued for an additional 30-45 minutes.
15. Preparation of Premix 2: To a suitable container about 5 mL of purified water, USP was added. To this container 60 mg of FD&C Red No. 40 was added while mixing using a suitable spatula until all contents were completely dissolved. End of Premix 2.
16. When the mixing of step 14 was completed, Premix 2 was added to the main container with mixing.
17. 3.0 grams of strawberry flavor 28082 (CW08) was added while mixing.
18. Mixing was continued for an additional 30-45 minutes.
19. The mixer was stopped and sufficient purified water, USP was added to make the final volume up to 2000 mL.
20. Mixing was continued for a further 10-15 minutes.
21. The batch was transferred to containers using bottle B325-38-BLA-WHT and cap 8040-A.

Example 3

Physicochemical properties and data characterizing the stability and homogeneity of omeprazole formulated to 2 mg/mL in the liquid diluent described above as Formula C0092 and Formula C0093 were determined as follows:

Omeprazole supplied by both suppliers were formulated to a 2 mg/mL nominal concentration in the liquid diluents as described above. At time zero, an initial assay in duplicate was made of the concentration of the API (omeprazole) in samples obtained from the top, middle (meaning midway between the surface of the liquid and the bottom of the container) and bottom of the container containing the formulated drug. The pH of the initial formulations were also determined by standard methods. The dynamic viscosity (6 rpm@25 degrees Celsius) was also determined for each initial formulation. Samples from the middle of a container of each formulation were further obtained after 2 and 15 days of storage at 5 degrees Celsius. After 30 days storage at 5 degrees Celsius, additional samples were obtained, again from the top, middle and bottom of the containers. Each of the samples was assayed in duplicate for omeprazole content, and the results are summarized in Tables 1 through 4 below.

TABLE 1

Omeprazole Supplier 1 in Formula C0092

| Sample Information | Sample Location | Assay ** | | pH | Viscosity |
|---|---|---|---|---|---|
| Initial | Top | 103.5 | 105.1 | 8.5 | 243.0 cP |
| | Middle | 103.0 | 103.7 | | |
| | Bottom | 103.6 | 104.1 | | |
| 2 days at 5° C. | Middle | 103.7 | 103.8 | | |
| 15 days at 5° C. | Middle | 102.9 | 103.3 | | |
| 30 days at 5° C. | Top | 103.2 | 102.3 | | |
| | Middle | 102.8 | 102.7 | | |
| | Bottom | 102.7 | 103.6 | | |

** Assay results are presented as the % recovery of the nominal concentration of the API. Thus a result of 100.5% would represent actual recovery of 2.01 mg/mL in the sample.

TABLE 2

Omeprazole Supplier 1 API in Formula C0093

| Sample Information | Sample Location | Assay ** | | pH | Viscosity |
|---|---|---|---|---|---|
| Initial | Top | 102.3 | 102.3 | 8.5 | 47.0 cP |
| | Middle | 101.8 | 103.2 | | |
| | Bottom | 103.8 | 102.9 | | |
| 2 days at 5° C. | Middle | 102.8 | 102.7 | | |
| 15 days at 5° C. | Middle | 102.5 | 102.1 | | |
| 30 days at 5° C. | Top | 102.3 | 102.4 | | |
| | Middle | 102.2 | 102.0 | | |
| | Bottom | 102.6 | 104.2 | | |

TABLE 3

Omeprazole Supplier 2 API in Formula C0092

| Sample Information | Sample Location | Assay ** | | pH | Viscosity |
|---|---|---|---|---|---|
| Initial | Top | 102.5 | 102.8 | 8.6 | 244.5 cP |
| | Middle | 101.9 | 107.2 | | |
| | Bottom | 102.9 | 103.5 | | |
| 2 days at 5° C. | Middle | 104.3 | 104.2 | | |
| 15 days at 5° C. | Middle | 103.8 | 105.0 | | |
| 30 days at 5° C. | Top | 104.4 | 104.1 | | |
| | Middle | 103.4 | 103.8 | | |
| | Bottom | 103.2 | 103.2 | | |

TABLE 4

Omeprazole Supplier 2 API in Formula C0093

| Sample Information | Sample Location | Assay ** | | pH | Viscosity |
|---|---|---|---|---|---|
| Initial | Top | 99.9 | 100.9 | 8.5 | 47.0 cP |
| | Middle | 100.8 | 98.1 | | |
| | Bottom | 105.2 | 101.3 | | |

TABLE 4-continued

Omeprazole Supplier 2 API in Formula C0093

| Sample Information | Sample Location | Assay ** | | pH | Viscosity |
|---|---|---|---|---|---|
| 2 days at 5° C. | Middle | 102.9 | 102.9 | | |
| 15 days at 5° C. | Middle | 101.7 | 102.2 | | |
| 30 days at 5° C. | Top | 101.1 | 101.5 | | |
| | Middle | 102.0 | 101.7 | | |
| | Bottom | 101.5 | 101.7 | | |

Example 4

Physicochemical properties and data characterizing the stability and homogeneity of lansoprazole formulated to 3 mg/mL in the liquid diluent described above as Formula C0092 and Formula C0093 were determined as follows:

Lansoprazole supplied by two different suppliers were formulated to a 3 mg/mL nominal concentration in the liquid diluents as described above. At time zero, an initial assay in duplicate was made of the concentration of the API (lansoprazole) in samples obtained from the top, middle (meaning midway between the surface of the liquid and the bottom of the container) and bottom of the container containing the formulated drug. The pH of the initial formulations were also determined by standard methods. The dynamic viscosity (6 rpm@25 degrees Celsius) was also determined for each initial formulation. Samples from the middle of a container of each formulation were further obtained after 15 days of storage at 5 degrees Celsius. After 30 days storage at 5 degrees Celsius, additional samples were obtained, again from the top, middle and bottom of the containers. Each of the samples was assayed in duplicate for lansoprazole content, and the results are summarized in Tables 5 through 8 below.

Lansoprazole Data

| | Time Point | | | | | | | | | | | | | |
|---|---|---|---|---|---|---|---|---|---|---|---|---|---|---|
| | Initial | | | | | | 15-days | | 30-days | | | | | | |
| | Formula 0092 | | | Formula 0093 | | | Formula 0092 | Formula 0093 | Formula 0092 | | | Formula 0093 | | |
| API | Assay | Average | RSD | Assay | Average | RSD | | | Assay | Average | RSD | Assay | Average | RSD |
| Moehs - top | 97.1 | 98.5 | 1.4% | 96.9 | 104.6 | 13.9% | — | — | 98.2 | 99.5 | 2.1% | 101.1 | 105.8 | 7.8% |
| Moehs - middle | 98.5 | | | 95.5 | | | 100.3 | 90.6 | 98.4 | | | 100.9 | | |
| Moehs - bottom | 99.9 | | | 121.3 | | | — | — | 102.0 | | | 115.3 | | |
| Dr. Reddy's - top | 98.4 | 98.2 | 0.2% | 98.7 | 98.6 | 0.2% | — | — | 100.6 | 100.3 | 0.3% | 98.0 | 100.1 | 3.5% |
| Dr. Reddy's - middle | 98.1 | | | 98.7 | | | 99.1 | 75.5 | 100.2 | | | 98.1 | | |
| Dr. Reddy's - bottom | 98.1 | | | 98.4 | | | — | — | 100.1 | | | 104.1 | | |

From these analyses, it was concluded that for up to 30 days of storage at refrigerated temperatures, neither formulation showed any significant decline in the assay value of the omeprazole or lansoprazole recoverable from the samples over the initial measurement. In addition, neither formulation showed any significant tendency to depart from a condition of homogeneous distribution of the PPIs in the container, i.e. there was no evidence of significant settling of the suspended API during the 30 days of storage. In addition, the accuracy of the formulation omeprazole and lansoprazole concentration, the pH, and viscosity of the initial formulations, and the stability and homogeneity over 30 days of storage were not impacted by the source of the API. Either formulation can be used to consistently deliver an accurate dose of respective PPI in a formulation of consistent pH and viscosity that remains stable and homogenous over a month of storage under refrigeration.

Example 5

Dissolution profiles were measured under standardized conditions in two media. When batches 0092-A and 0092-B were compared to Zegerid 40 mg (PBZD) reconstituted in a media of phosphate buffered to physiological pH (i.e. pH 7.4), the dissolution profiles of 0092-A and 0092-B were highly consistent, showing bolus dissolution of API at the first measurement point (5 minutes) where 96-97% of the API had dissolved, and essentially no further recovery over 30 minutes of dissolution testing. Under the same conditions, Zegerid performed similarly with 93% of API dissolved after 5 minutes, climbing slightly to 96% over the 30 minutes study.

On the other hand, when 0092A and Zegerid 40 mg (PBZD) reconstituted were compared in biorelevant media (0.01 N HCL, i.e. approximately pH 2.0 or the pH of normal human stomach acid), both formulations showed rapid dissolution with peak API concentration released reached with the first five minutes. However, the two formulations plateaued at different maxima. While approximately 92% of 0092-A API was recovered, just 88% of the Zegerid API was recovered. Even after 30 minutes of mixing, no more than 85-88% of the Zegerid API was measured in solution.

REFERENCES

Burnett J. E. and Balkin E. R. Stability and viscosity of a flavored omeprazole oral suspension for pediatric use. Am J Health Syst Pharm. 2006 Nov. 15; 63(22):2240-7.
Johnson, C. E., Cober, M. P., and Ludwig, J. L. Stability of partial doses of omeprazole-sodium bicarbonate oral suspension. Ann Pharmacother. 2007 December; 41(12): 1954-61. Epub 2007 Oct. 23.
United States Pharmacopeia and the National Formulary (2016) 39$^{th}$ Edition (USP) 34$^{th}$ Edition (NF)
Sharma, V. K., Peyton, B., Spears, T., Raufman, J. P., and Howden, C. W. Oral pharmacokinetics of omeprazole and lansoprazole after single and repeated doses as intact capsules or as suspensions in sodium bicarbonate. Aliment Pharmacol Ther. 2000 July; 14(7): 887-92.
Sharma, V. K. Comparison of 24-hour intragastric pH using four liquid formulations of lansoprazole and omeprazole. Am J Health Syst Pharm. 1999 Dec. 1; 56(23 Suppl 4):S18-21.
Castell, D. Review of immediate-release omeprazole for the treatment of gastric acid-related disorders. Expert Opin Pharmacother. 2005 November; 6(14):2501-10.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. An oral liquid suspension of a proton pump inhibitor (PPI), comprising:
    a PPI, wherein the PPI is omeprazole and is present at 2 mg/ml in the suspension;
    0.4%-0.6% (w/v) benzyl alcohol;
    1.0%-6.0% (w/v) a copolymer of ethylene oxide and propylene oxide;
    0.1%-0.3% (w/v) simethicone emulsion (30%);
    8.0%-8.8% (w/v) sodium bicarbonate;
    0.5%-1.5% (w/v) sodium citrate (dihydrate);
    a sweetener that comprises ammonium glycyrrhizate and sucralose;
    a thickening agent that is xanthan gum or hydroxyethylcellulose; and
    water,
    wherein the pH of the suspension is at least pH 8.0, and wherein the formulation retains homogeneity of less than +/−5% of variation for the omeprazole by assay after at least 30 days stored at 5° C.
2. The suspension of claim 1, wherein the copolymer of ethylene oxide and propylene oxide is Poloxamer 188.
3. The suspension of claim 1, wherein the sweetener further comprises sorbitol.
4. The suspension of claim 1, further comprising propylene glycol.
5. The suspension of claim 1, further comprising FD&C Red No. 40, or strawberry flavor.
6. The suspension of claim 1, wherein the dynamic viscosity is greater than or equal to 50 and less than or equal to 1000 centipoise (cP) when determined at 6 rpm and 25° C.
7. The suspension of claim 1, wherein the dynamic viscosity is greater than or equal to 40 and less than or equal to 50 centipoise (cP) when determined at 6 rpm and 25° C.
8. The suspension of claim 1, wherein the dynamic viscosity is greater than or equal to 200 and less than or equal to 300 centipoise (cP) when determined at 6 rpm and 25° C.
9. The suspension of claim 1, wherein the suspension includes the following:
    a. 0.5% (w/v) benzyl alcohol;
    b. 0.003% (w/v) FD&C Red No. 40;
    c. 0.15% (w/v) strawberry flavor;
    d. 0.35% (w/v) hydroxyethylcellulose;
    e. 2.00-4.00% (w/v) Poloxamer 188;
    f. 5.0% (w/v) propylene glycol;
    g. 0.2% (w/v) simethicone emulsion (30%);
    h. 8.4% (w/v) sodium bicarbonate;
    i. 1.0% (w/v) sodium citrate (dihydrate);
    j. ammonium glycyrrhizate and 0.45% (w/v) sucralose;
    k. 0.4% (w/v) xanthan gum; and
    l. purified water.
10. The suspension of claim 1, wherein the suspension includes the following:

a. 0.5% (w/v) benzyl alcohol;
b. 0.003% (w/v) FD&C Red No. 40;
c. 0.15% (w/v) strawberry flavor;
d. 0.07% (w/v) ammonium glycyrrhizate;
e. 0.25% (w/v) hydroxyethylcellulose;
f. 2.0% (w/v) Poloxamer 188;
g. 0.08% (w/v) saccharin sodium;
h. 0.2% (w/v) simethicone emulsion (30%);
i. 8.4% (w/v) sodium bicarbonate;
j. 1.0% (w/v) sodium citrate (dihydrate);
k. 2.5% (w/v) sorbitol solution (70%);
l. 0.4% (w/v) sucralose; and
m. purified water.

11. The suspension of claim 1, wherein the suspension is stable for at least 30 days when stored at 2-8 degrees Celsius.

12. The suspension of claim 1, wherein the suspension comprises the following:
omeprazole that is present at 2 mg/ml in the suspension;
0.4%-0.6% (w/v) benzyl alcohol;
0.2%-0.5% (w/v) hydroxyethylcellulose;
1.0%-6.0% (w/v) Poloxamer 188;
0.1%-0.3% (w/v) simethicone emulsion (30%);
8.0%-8.8% (w/v) sodium bicarbonate;
0.5%-1.5% (w/v) sodium citrate (dihydrate);
ammonium glycyrrhizate and 0.35%-0.5% (w/v) sucralose;
1.5%-4% (w/v) sorbitol solution; and
8%-12% (w/v) glycerin 99.7%.

13. The suspension of claim 12, wherein the suspension consists essentially of the following:
omeprazole that is present at 2 mg/ml in the suspension;
0.4%-0.6% (w/v) benzyl alcohol;
0.002%-0.005% (w/v) FD&C Red No. 40;
0.1%-0.2% (w/v) strawberry flavor;
0.2%-0.5% (w/v) hydroxyethylcellulose;
1.0%-6.0% (w/v) Poloxamer 188;
0.1%-0.3% (w/v) simethicone emulsion (30%);
8.0%-8.8% (w/v) sodium bicarbonate;
0.5%-1.5% (w/v) sodium citrate (dihydrate);
ammonium glycyrrhizate and 0.35%-0.5% (w/v) sucralose;
purified water;
1.5%-4% (w/v) sorbitol solution; and
8%-12% (w/v) glycerin 99.7%.

14. The suspension of claim 12, wherein the suspension consists essentially of the following:
omeprazole that is present at 2 mg/ml in the suspension;
0.5% (w/v) benzyl alcohol;
0.003% (w/v) FD&C Red No. 40;
0.15% (w/v) strawberry flavor;
0.35% (w/v) hydroxyethylcellulose;
2.0% (w/v) Poloxamer 188;
0.15% (w/v) simethicone emulsion (30%);
8.4% (w/v) sodium bicarbonate;
1.0% (w/v) sodium citrate (dihydrate);
ammonium glycyrrhizate and 0.4% (w/v) sucralose;
purified water;
2.5% (w/v) sorbitol solution; and
10% (w/v) glycerin 99.7%.

15. The suspension of claim 12, wherein the suspension consists essentially of the following:
omeprazole that is present at 2 mg/ml in the suspension;
0.5% (w/v) benzyl alcohol;
0.003% (w/v) FD&C Red No. 40;
0.15% (w/v) strawberry flavor;
0.35% (w/v) hydroxyethylcellulose;
4.0% (w/v) Poloxamer 188;
0.15% (w/v) simethicone emulsion (30%);
8.4% (w/v) sodium bicarbonate;
1.0% (w/v) sodium citrate (dihydrate);
ammonium glycyrrhizate and 0.4% (w/v) sucralose;
purified water;
2.5% (w/v) sorbitol solution; and
10% (w/v) glycerin 99.7%.

16. The suspension of claim 1, wherein the suspension consists essentially of the following:
omeprazole that is present at 2 mg/ml in the suspension;
0.4-0.6% (w/v) benzyl alcohol;
0.002-0.005% (w/v) dye;
0.1-0.2% (w/v) flavoring;
0.06-0.08% (w/v) ammonium glycyrrhizate;
1.00-3.00% (w/v) Poloxamer 188;
4.0-6.0% (w/v) propylene glycol;
0.1-0.3% (w/v) simethicone emulsion;
8.0-8.8% (w/v) sodium bicarbonate;
0.5-1.5% (w/v) sodium citrate (dihydrate);
0.4-0.45% (w/v) sucralose;
0.3-0.5% (w/v) xanthan gum; and
purified water.

17. The suspension of claim 1, wherein the suspension consists essentially of the following:
omeprazole that is present at 2 mg/ml in the suspension;
0.5% (w/v) benzyl alcohol;
0.003% (w/v) FD&C Red No. 40;
0.15% (w/v) strawberry flavor;
0.07% (w/v) ammonium glycyrrhizate;
2.00% (w/v) Poloxamer 188;
5.0% (w/v) propylene glycol;
0.2% (w/v) simethicone emulsion (30%);
8.4% (w/v) sodium bicarbonate;
1.0% (w/v) sodium citrate (dihydrate);
0.45% (w/v) sucralose;
0.4% (w/v) xanthan gum; and
purified water.

* * * * *